United States Patent
Yamashita et al.

(10) Patent No.: US 9,161,702 B2
(45) Date of Patent: Oct. 20, 2015

(54) ELECTRONIC SPHYGMOMANOMETER

(75) Inventors: Shingo Yamashita, Kyoto (JP); Akira Tsuji, Ritto (JP); Hiroyasu Ariga, Kyoto (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 345 days.

(21) Appl. No.: 13/162,278

(22) Filed: Jun. 16, 2011

(65) Prior Publication Data
US 2011/0245696 A1    Oct. 6, 2011

Related U.S. Application Data

(63) Continuation of application No. PCT/JP2009/070472, filed on Dec. 7, 2009.

(30) Foreign Application Priority Data

Dec. 17, 2008    (JP) .................... 2008-321471

(51) Int. Cl.
*A61B 5/02*     (2006.01)
*A61B 5/022*    (2006.01)
*H02J 7/00*     (2006.01)

(52) U.S. Cl.
CPC ..... *A61B 5/02233* (2013.01); *A61B 2560/0204* (2013.01); *A61B 2560/0214* (2013.01); *A61B 2560/0242* (2013.01); *H02J 7/0013* (2013.01); *H02J 2007/0067* (2013.01)

(58) Field of Classification Search
USPC ................................ 600/485–525
See application file for complete search history.

(56) References Cited

U.S. PATENT DOCUMENTS

| | | | | |
|---|---|---|---|---|
| 4,969,466 A | * | 11/1990 | Brooks | 600/494 |
| 5,711,302 A | * | 1/1998 | Lampropoulos et al. | 600/485 |
| 2004/0095116 A1 | * | 5/2004 | Kernahan et al. | 323/282 |
| 2006/0155196 A1 | * | 7/2006 | Ramsey | 600/490 |
| 2007/0150019 A1 | * | 6/2007 | Youker et al. | 607/29 |
| 2008/0231226 A1 | * | 9/2008 | Hoffman et al. | 320/103 |
| 2010/0231175 A1 | * | 9/2010 | Noda | 320/162 |

FOREIGN PATENT DOCUMENTS

| | | | |
|---|---|---|---|
| JP | 63-113223 U | | 7/1988 |
| JP | 63-113223 U | * | 7/1988 |
| JP | H02-035707 U | | 3/1990 |
| JP | 03-075035 A | | 3/1991 |
| JP | 05-145463 A | | 6/1993 |

(Continued)

OTHER PUBLICATIONS

International Search Report issued in PCT/JP2009/070472 mailed on Dec. 28, 2009, and English translation thereof, 4 pages.

(Continued)

*Primary Examiner* — Michael Kahelin
*Assistant Examiner* — Mitchell E Alter
(74) *Attorney, Agent, or Firm* — Osha Liang LLP

(57) ABSTRACT

A power supply unit of an electronic sphygmomanometer includes a dry cell as a primary battery, a rechargeable battery as a secondary battery, and a power supply control circuit. A voltage detector detects a voltage (characteristic value) of the rechargeable battery, and a voltage detector detects the voltage of the dry cell. A switching control unit performs switching control of the dry cell and the rechargeable battery based on a detection result by the voltage detectors.

8 Claims, 16 Drawing Sheets

(56) References Cited

FOREIGN PATENT DOCUMENTS

| JP | H05-235823 A | 9/1993 |
|---|---|---|
| JP | 09-038047 A | 2/1997 |
| JP | 2001-245857 A | 9/2001 |

OTHER PUBLICATIONS

Patent Abstracts of Japan, Publication No. 2001-245857, Publication Date: Sep. 11, 2001, 1 page.
Patent Abstracts of Japan, Publication No. 05-145463, Publication Date: Jun. 11, 1993, 1 page.
Patent Abstracts of Japan, Publication No. 09-038047, Publication Date: Feb. 10, 1997, 1 page.
Patent Abstracts of Japan, Publication No. 03-075035, Publication Date: Mar. 29, 1991, 1 page.
Chinese First Office Action with translation mailed on Jan. 28, 2013, issued for Chinese Patent Application No. 200980151141.0 (12 pages).
Office Action issued in corresponding Russian Application No. 2011129623/14(043839) dated Nov. 28, 2013, and English translation thereof (7 pages).

* cited by examiner

| Display | Residual quantity of voltage |
|---|---|
|  | Level 3 |
|  | Level 2 |
|  | Level 1 |
|  | Level 0 (battery low) |

ELECTRONIC SPHYGMOMANOMETER

TECHNICAL FIELD

The present invention relates to an electronic sphygmomanometer, and in particular, relates to an electronic sphygmomanometer including a battery.

BACKGROUND ART

Measuring a blood pressure every day is very important from the perspective of health care. Thus, electronic sphygmomanometers for home use that can measure a blood pressure also outside the hospital are widely used.

An electronic sphygmomanometer is driven by a primary battery (hereinafter, referred to as a "dry cell"), an AC (Alternating Current) adapter, or a secondary battery (hereinafter, referred to as a "rechargeable battery").

However, if one of the dry cell and the rechargeable battery is used, a blood pressure cannot be measured if the capacity (residual quantity) thereof runs out during measurement.

Thus, Japanese Unexamined Patent Publication No. 2001-245857 (Patent Document 1) proposes a technique to let a user know the remaining number of times of measurement based on the voltage value of the battery.

Patent Document 1: Japanese Unexamined Patent Publication No. 2001-245857

SUMMARY OF INVENTION

However, consumption of battery capacity is affected by a pressurization time of a pump depending on a size around an arm and a blood pressure value (maximal blood pressure) and an ambient temperature, which makes it difficult to accurately indicate the remaining number of times of measurement. Therefore, according to the conventional technique, a dry cell may be replaced or a rechargeable battery may be charged if measurement can still be made. Conversely, if the number of times of measurement is one or more, measurement may not be continued due to insufficient capacity during measurement.

When a rechargeable battery is charged by solar energy, the rechargeable battery may not be quickly charged depending on conditions of usage.

When a cuff is pressurized (beginning of pressurization), the voltage drops considerably due to driving of the pump. Thus, if the voltage value of the battery when the measurement starts is below a predetermined voltage capable of driving a pump, a battery replacement mark or a charging mark is indicated. In such a case, therefore, the residual quantity of the dry cell or rechargeable battery cannot be used up. If the rechargeable battery is repeatedly charged while there is a sufficient residual quantity, the life of the rechargeable battery is reduced so that it is desirable to use up the residual quantity as much as possible also for the rechargeable battery.

Therefore, one or more embodiments of the present invention provides an electronic sphygmomanometer that can be used whenever the user desires to measure the blood pressure and that is capable of using the battery efficiently.

An electronic sphygmomanometer according to one or more embodiments of the present invention is an electronic sphygmomanometer for measuring a blood pressure of a person to be measured, including a cuff to be wrapped around a predetermined body site of the person to be measured, a pressure sensor for detecting a pressure inside the cuff, a measurement control unit for controlling blood pressure measurement of the person to be measured based on a signal from the pressure sensor, a power supply unit that includes a primary battery and a secondary battery, a plurality of characteristic value detectors for detecting a characteristic value of each of the primary battery and the secondary battery, a plurality of pressurization units for pressurizing the cuff using power supplied from the power supply unit, and a switching control unit for selecting a supply source of the power to operate the electronic sphygmomanometer by switching the primary battery and the secondary battery. The characteristic value is a value related to a residual quantity of each of the primary battery and the secondary battery.

The switching control unit compares the characteristic value detected by the plurality of characteristic value detectors and a first threshold upon startup of the electronic sphygmomanometer, selects the primary battery or the secondary battery based on a comparison result, compares the characteristic value detected by the plurality of characteristic value detectors and a second threshold larger than the first threshold before pressurization by the plurality of pressurization units after the startup, and selects the primary battery or the secondary battery based on the comparison result.

According to one or more embodiments of the present invention, the electronic sphygmomanometer further includes a solar battery for receiving sunlight and converting received light energy into electric energy, wherein the secondary battery stores the electric energy generated by the solar battery.

According to one or more embodiments of the present invention, the switching control unit makes a weather forecast based on the signal from the pressure sensor and selects the primary battery or the secondary battery based on a weather forecast result.

According to one or more embodiments of the present invention, when the characteristic value of the secondary battery is larger than a first threshold upon startup of the electronic sphygmomanometer, when the switching control unit selects the secondary battery, and when the characteristic value of the secondary battery is equal to or smaller than the first threshold, the switching control unit selects the primary battery or the secondary battery in accordance with the weather forecast result.

According to one or more embodiments of the present invention, when the characteristic value of the primary battery, which is set to be used preferentially of the primary battery and the secondary battery, is larger than the first threshold upon startup of the electronic sphygmomanometer, the switching control unit selects the primary battery, and when the characteristic value of the primary battery is equal to or smaller than the first threshold, the switching control unit includes a first selection processing unit for selecting the secondary battery, which is the other battery.

According to one or more embodiments of the present invention, when the primary battery is selected upon startup of the electronic sphygmomanometer, the switching control unit further switches from the primary battery to the secondary battery when the switching control unit determines that the characteristic value of the primary battery detected by the plurality of characteristic value detectors before pressurization by the pressurization units is equal to or smaller than the second threshold.

According to one or more embodiments of the present invention, when the secondary battery is selected by a second selection processing unit before pressurization, the switching control unit further switches from the secondary battery to the primary battery again when the switching control unit determines that the voltage of the primary battery during the pressurization by the plurality of pressurization units is larger than a third threshold that is smaller than the second threshold.

The third threshold may be a value equal to the first threshold or a value larger than the first threshold.

According to one or more embodiments of the present invention, the switching control unit preferentially selects the battery specified by a user in advance of the primary battery and the secondary battery.

According to one or more embodiments of the present invention, the electronic sphygmomanometer further includes a generation unit for generating an alarm sound in a specific timing specified by a user, wherein when the specific timing comes, the switching control unit further switches the primary battery and the secondary battery based on the detection results by the plurality of characteristic value detectors.

According to one or more embodiments of the present invention, the characteristic value represents any of a voltage value, a voltage level based on the voltage value, and the number of times of measurement calculated from the voltage value.

An electronic sphygmomanometer according to one or more embodiments of the present invention is an electronic sphygmomanometer for measuring a blood pressure of a person to be measured, including: a cuff to be wrapped around a predetermined body site of the person to be measured, a pressure sensor for detecting a pressure inside the cuff, a measurement control unit for controlling blood pressure measurement of the person to be measured based on a signal from the pressure sensor, a solar battery for receiving sunlight and converting received light energy into electric energy, a power supply unit that includes a primary battery and a secondary battery for storing the electric energy generated by the solar battery, and a switching control unit for selecting a supply source of power to operate the electronic sphygmomanometer by switching the primary battery and the secondary battery, wherein the switching control unit makes a weather forecast based on the signal from the pressure sensor and selects the primary battery or the secondary battery in accordance with a result of the weather forecast.

According to one or more embodiments of the present invention, the electronic sphygmomanometer further includes a plurality of characteristic value detectors for detecting a characteristic value of each of the primary battery and the secondary battery, wherein the characteristic value is a value related to a residual quantity of each of the primary battery and the secondary battery, and the switching control unit selects the secondary battery when the characteristic value of the secondary battery detected by the characteristic value detectors is larger than a first threshold upon startup of the electronic sphygmomanometer, and selects the primary battery or the secondary battery in accordance with the result of the weather forecast when the characteristic value of the secondary battery is equal to or smaller than the first threshold.

According to one or more embodiments of the present invention, the electronic sphygmomanometer includes a primary battery and a secondary battery, and both can be switched based on a characteristic value related to the residual quantity thereof. Therefore, a situation in which measurement cannot be made unexpectedly can be avoided. Moreover, residual quantities of both batteries can be used efficiently.

DETAILED DESCRIPTION OF INVENTION

Figure 1:
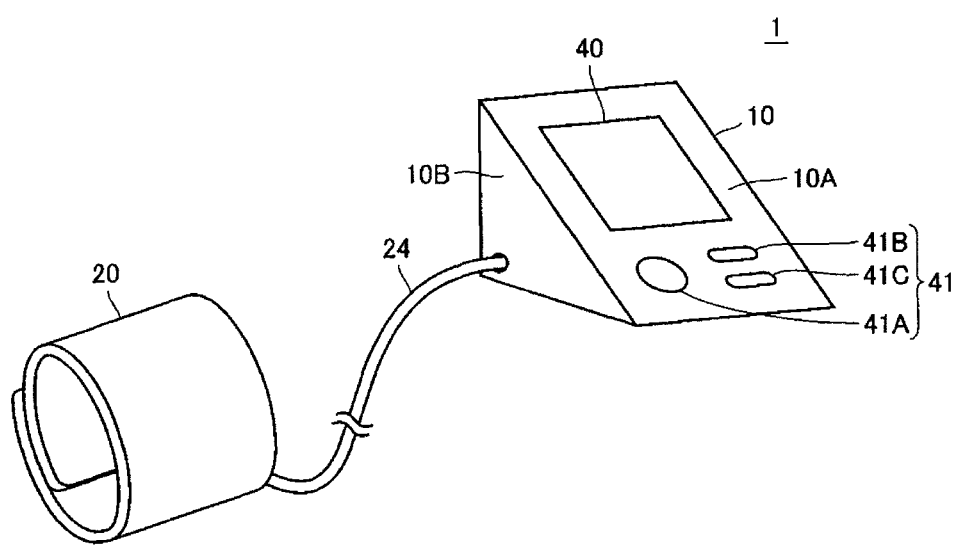
FIG. 1 is a diagram showing an appearance of an electronic sphygmomanometer according to one or more embodiments of the present invention.

Embodiments of the present invention will be described in detail with reference to the drawings. The same reference numerals are attached to the same or equivalent elements in the drawings and a description thereof will not be repeated.

[First Embodiment]

<Regarding Appearance and Configuration>

(Regarding Appearance)

First, an appearance of an electronic sphygmomanometer (hereinafter, referred to as a "sphygmomanometer" for short) 1 according to the present embodiment will be described with reference to FIGS. 1 and 2.

FIG. 1 is a diagram showing the appearance of the sphygmomanometer 1 according to the first embodiment of the present invention.

Referring to FIG. 1, the sphygmomanometer 1 includes a main body portion 10, a cuff 20 to be wrapped around, for example, an upper arm of a person to be measured, and an air tube 24 to connect the main body portion 10 and the cuff 20.

Figure 2:
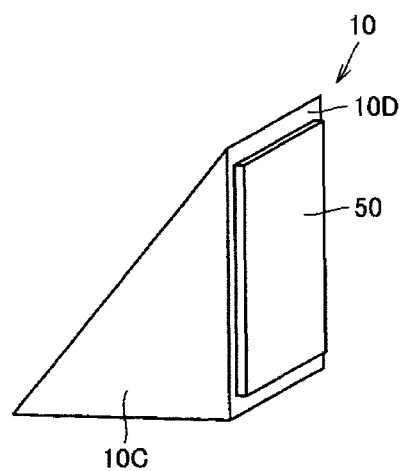
FIG. 2 is a perspective view of a main body portion of the electronic sphygmomanometer according to one or more embodiments of the present invention viewed from a rear direction.

FIG. 2 is a perspective view of the main body portion 10 according to the first one or more embodiments of the present invention viewed from a rear direction.

Referring to FIGS. 1 and 2, the main body portion 10 is a pentahedron and includes an installation surface in contact with a base such as a desk, a surface 10A forming a predetermined angle with the installation surface, two side surfaces 10B, 10C that are surfaces perpendicular to the installation surface, and a rear surface 10D.

A display unit 40 for displaying measurement results and the like and an operation unit 41 for receiving input of an instruction from a user (typically, a person to be measured) are arranged on the surface 10A of the main body portion 10. The operation unit 41 includes, for example, a power switch 41A for switching ON/OFF of the power supply, a measurement switch 41B for inputting an instruction to start measurement, and a memory switch 41C for inputting an instruction to read and display past measurement results.

The display unit 40 is made of, for example, a liquid crystal display.

The air tube 24 is connected to the left side surface 10B of the main body portion 10.

A solar battery (solar panel) 50 is arranged on the rear surface 10D of the main body portion 10. Thus, if the sphygmomanometer 1 is placed in a location where outside light is brought in, such as near a window inside a room, the solar battery 50 receives sunlight and converts the received light energy into electric energy. That is, the solar battery 50 generates electric energy in accordance with an amount of received light. The generated electric energy is outputted to a rechargeable battery (secondary battery) 51 (see FIG. 3) contained in the main body portion 10.

The shape of the main body portion 10 of the sphygmomanometer 1 is not limited to the shape of such an example.

(Regarding Hardware Configuration)

Figure 3:
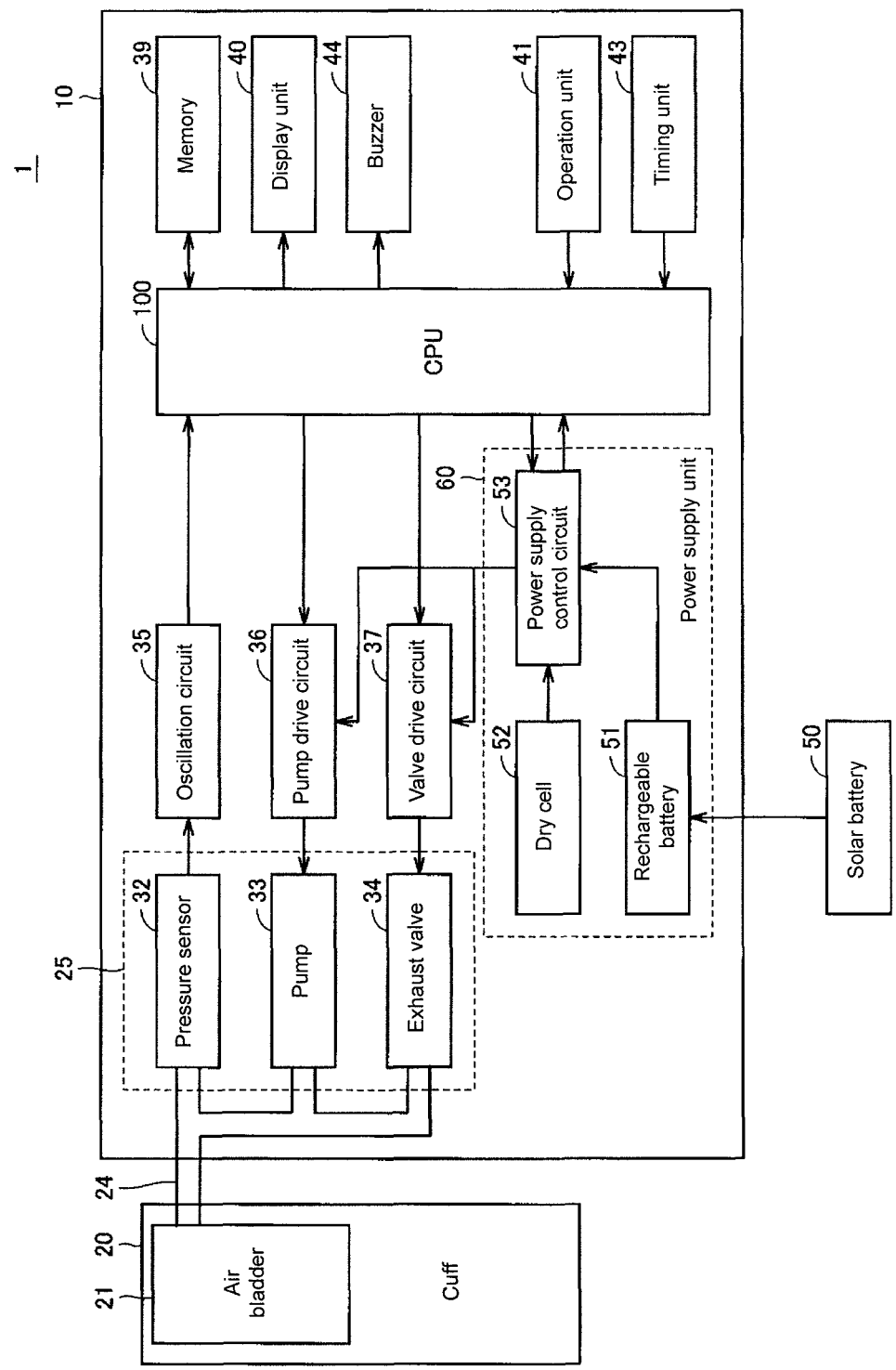
FIG. 3 is a block diagram showing a hardware configuration of the electronic sphygmomanometer according to one or more embodiments of the present invention.

FIG. 3 is a block diagram showing the hardware configuration of the sphygmomanometer 1 according to the first one or more embodiments of the present invention.

Referring to FIG. 3, the cuff 20 of the sphygmomanometer 1 includes an air bladder 21 enclosing air therein. The air bladder 21 is connected to an air system 25 contained in the main body portion 10 via the air tube 24.

The air system 25 includes a pressure sensor 32 for detecting the pressure inside the air bladder 21 (hereinafter, referred to as a "cuff pressure"), a pump 33 for supplying air into the air bladder 21, and an exhaust valve 34 that is opened/closed to exhaust or enclose air in the air bladder 21.

The main body portion 10 includes a CPU (Central Processing Unit) 100 for centrally controlling and monitoring each unit, a nonvolatile memory 39, the display unit 40, the operation unit 41, a power supply unit 60, a timing unit 43 for measuring the time, and a buzzer 44 for generating an alarm sound. The main body portion 10 further includes a pump drive circuit 36 for driving an oscillation circuit 35 and the pump 33 related to the air system 25, and a valve drive circuit 37 for driving the exhaust valve 34.

The pump drive circuit 36 controls driving of the pump 33 based on a control signal provided from the CPU 100. The valve drive circuit 37 controls opening/closing of the exhaust valve 34 based on a control signal provided from the CPU 100.

The capacity value of the pressure sensor 32 changes depending on the cuff pressure. The oscillation circuit 35 outputs a signal of the oscillating frequency in accordance with the capacity value of the pressure sensor 32 to the CPU 100. The CPU 100 detects the pressure by converting the signal obtained from the oscillation circuit 35 into a pressure.

The memory 39 stores various programs and various kinds of data. The memory 39 includes a measurement result storage area for storing measurement results of the blood pressure.

The power supply unit 60 includes a rechargeable battery 51 for storing electric energy generated by the solar battery 50, a removable dry cell (primary battery) 52, and a power supply control circuit 53. The power supply unit 60 may further include an AC adapter (not shown) for quickly charging the rechargeable battery 51.

The power supply control circuit 53 is electrically connected to the rechargeable battery 51 and the dry cell 52, and selectively supplies power stored in the rechargeable battery 51 and the dry cell 52 to various devices such as the pump drive circuit 36 and the valve drive circuit 37. The power supply control circuit 53 is electrically connected to the CPU 100 to transmit/receive signals to/from the CPU 100. A configuration example of the power supply control circuit 53 will be described later.

The rechargeable battery 51 is, for example, nickel hydrogen battery. The dry cell 52 is, for example, an alkaline battery.

(Regarding Functional Configuration)

Figure 4:
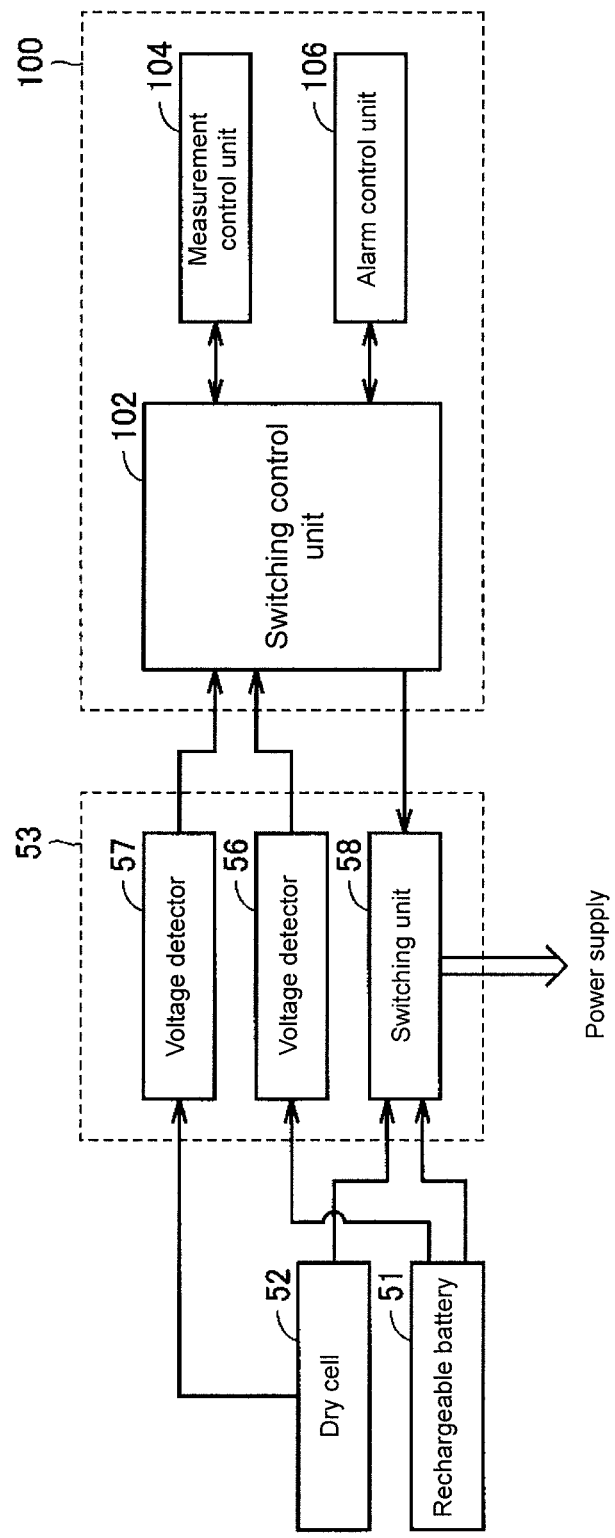
FIG. 4 is a functional block diagram of the electronic sphygmomanometer according to one or more embodiments of the present invention.

FIG. 4 is a functional block diagram of the sphygmomanometer 1 in the first embodiment of the present invention.

Referring to FIG. 4, the power supply control circuit 53 includes a voltage detector 56 for detecting the voltage of the rechargeable battery 51, a voltage detector 57 for detecting the voltage of the dry cell 52, and a switching unit 58 for switching the output of the rechargeable battery 51 and the dry cell 52.

Generally, the residual quantity of a battery can be detected (estimated) based on the voltage. Thus, also in the present embodiment, the voltage is to be detected as a characteristic value related (correlated) to the residual quantity of each of the batteries 51, 52. However, the characteristic value is not limited to the voltage as long as it is correlated with the residual quantity.

The switching unit 58 is made of, for example, a switch.

In the present embodiment, the voltage detectors 56, 57 are included in the power supply control circuit 53 of the power supply unit 60, but they may be provided independently of the power supply unit 60.

The CPU 100 includes, as functions thereof, a switching control unit 102, a measurement control unit 104, and an alarm control unit 106.

The switching control unit 102 performs switching control of the rechargeable battery 51 and the dry cell 52 based on voltage values detected by the voltage detectors 56, 57. More specifically, the switching unit 58 is caused to select one of the rechargeable battery 51 and the dry cell 52 by sending a control signal to the switching unit 58. A detailed description of the switching control will be given later.

The measurement control unit 104 controls the pump drive circuit 36 and the valve drive circuit 37 shown in FIG. 3. The measurement control unit 104 calculates blood pressure values (for example, the maximal blood pressure and minimal blood pressure) based on a signal (cuff pressure signal) from the oscillation circuit 35 shown in FIG. 3 according to, for example, an oscillometric method. Also, the measurement control unit 104 calculates a pulse rate according to a publicly known method.

The alarm control unit 106 is connected to the buzzer 44 shown in FIG. 3 and performs control so that an alarm sound is generated in a specific timing (for example, the date and time) specified by the user.

The operation of each functional block may be realized by executing software stored in the memory 39, or at least one of these functional blocks may be realized by hardware.

<Regarding Operation>

The operation of the sphygmomanometer 1 according to the present embodiment will be described.

In the following description, it is assumed that information indicating a mode to preferentially use the rechargeable battery 51, i.e., a rechargeable battery preference mode is stored in the memory 39. The battery to be used preferentially may be set by default in advance when the sphygmomanometer 1 is shipped. Alternatively, the user may be enabled to specify (set and change) the battery to be used preferentially by operating the operation unit 41.

Figure 5:
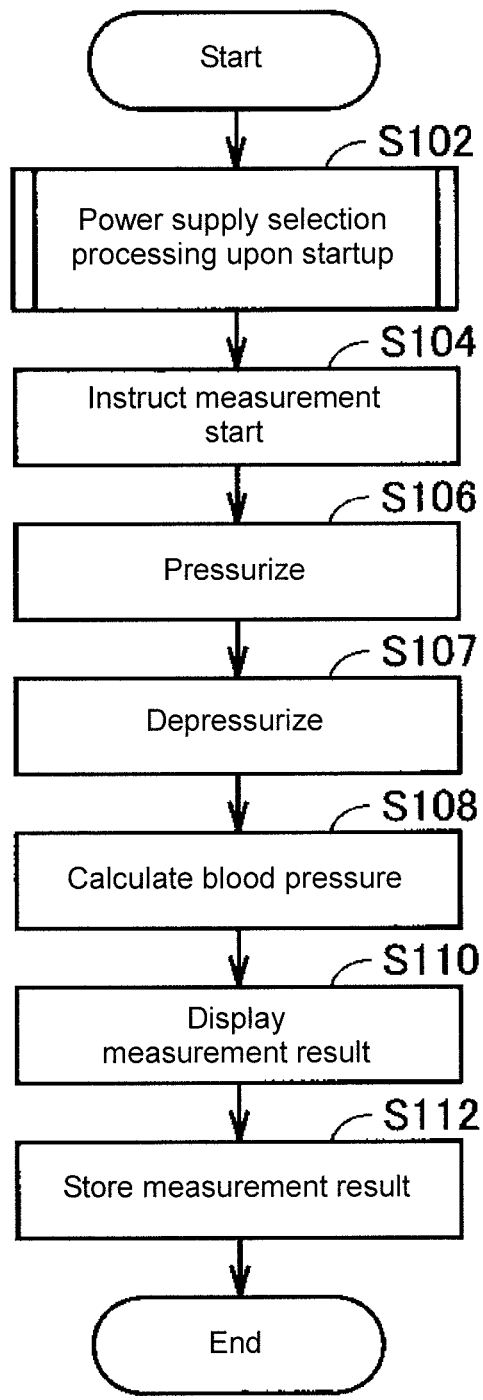
FIG. 5 is a flowchart showing measurement related processing according to a first embodiment of the present invention.

FIG. 5 is a flowchart showing processing performed by the CPU 100 regarding measurement control of the blood pressure (hereinafter, referred to as "measurement related processing") in the first embodiment of the present invention. The processing shown in the flowchart of FIG. 5 is stored in the memory 39 as a program in advance, and the CPU 100 reads and executes the program.

Referring to FIG. 5, if the power switch 41A is pressed, first, power supply selection processing upon startup is performed (step S102). The processing will be described in detail as a subroutine in FIG. 6.

Figure 6:
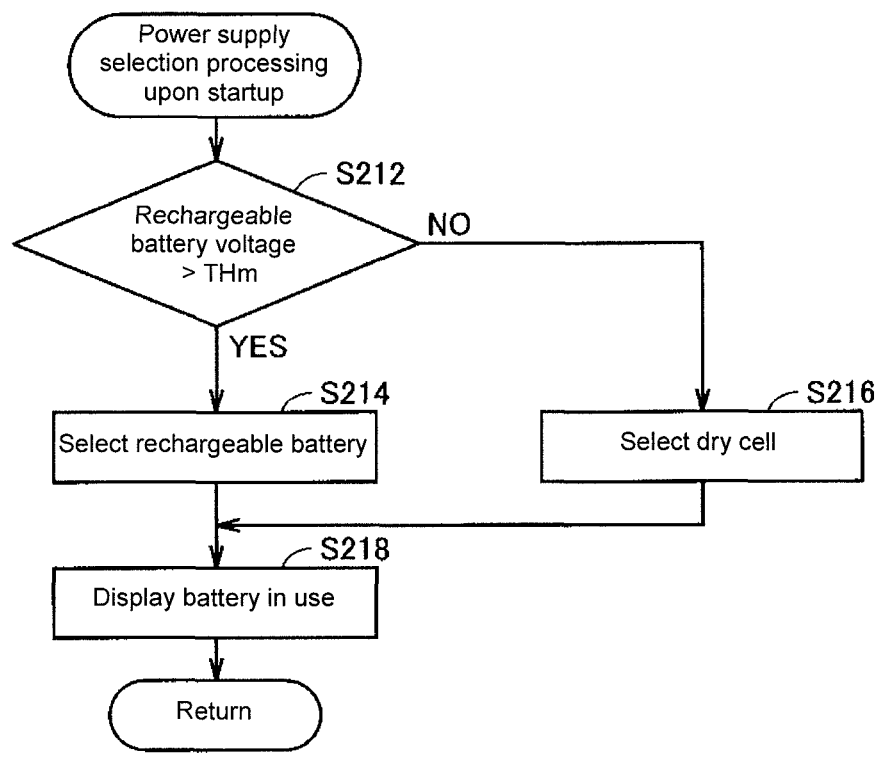
FIG. 6 is a flowchart showing power supply selection processing according to the first embodiment of the present invention.

FIG. 6 is a flowchart showing the power supply selection processing in the first embodiment of the present invention.

In the following description, first, it is assumed that the rechargeable battery 51 is selected by the switching unit 58. It is also assumed that the dry cell 52 has a sufficient residual quantity. That is, the voltage of the dry cell 52 obtained from the voltage detector 57 is assumed to be equal to or more than a threshold THm (for example, 4.5 V) described later.

Referring to FIG. 6, the switching control unit 102 determines whether the voltage of the rechargeable battery 51 is larger than the predetermined threshold THm (step S212). The voltage of the rechargeable battery 51 is obtained from output of the voltage detector 56 shown in FIG. 4.

The threshold THm may be any value equal to or greater than a voltage necessary for at least one time accomplishment of blood pressure measurement processing. Here, for example, the threshold THm is a value obtained by adding a predetermined value to the voltage necessary for one time accomplishment of blood pressure measurement processing.

If the voltage of the rechargeable battery 51 is larger than the threshold THm (YES in step S212), the switching control unit 102 selects the rechargeable battery 51 (step S214). The rechargeable battery 51 is already selected at the beginning of the processing and thus, in this case, the switching control unit 102 does not switch the power supply.

On the other hand, if the voltage of the rechargeable battery 51 is equal to or less than the threshold THm (NO in step S212), the switching control unit 102 selects the dry cell 52 (step S216). In this case, the switching control unit 102 performs switching processing of the power supply. That is, the switching control unit 102 sends a control signal to the switching unit 58 to select the dry cell 52.

In step S216, the CPU 100 notifies to charge the rechargeable battery 51 according to one or more embodiments of the present invention.

When the processing in step S214 or step S216 ends, the switching control unit 102 displays which of the rechargeable battery 51 and the dry cell 52 is the battery in use in the display unit 40 (step S218).

When this processing ends, the processing returns to the main routine.

Referring to FIG. 5 again, if the power supply selection processing upon startup is completed and the measurement switch 41B is pressed, an instruction to start measurement is inputted (step S104).

Then, the measurement control unit 104 starts to drive the pump 33 to gradually raise the pressure of the air bladder 21 (step S106). If the rechargeable battery 51 has been selected by the switching unit 58 of the power supply control circuit 53, power stored in the rechargeable battery 51 becomes the driving source of the pump 33. If the dry cell 52 has been selected by the switching unit 58 of the power supply control circuit 53, power stored in the dry cell 52 becomes the driving source of the pump 33.

If the cuff pressure reaches the predetermined level for measurement of the blood pressure, the measurement control unit 104 stops the pump 33 and gradually opens the closed exhaust valve 34 to gradually exhaust the air of the air bladder 21. Accordingly, the cuff pressure is gradually reduced (step S107).

Next, the measurement control unit 104 calculates the blood pressure (the maximal blood pressure and minimal blood pressure) by a publicly known method (step S108). More specifically, in the process in which the cuff pressure is gradually reduced, the measurement control unit 104 extracts pulse wave information based on the oscillating frequency obtained from the oscillation circuit 35. Then, the measurement control unit 104 calculates the blood pressure from the extracted pulse wave information. The measurement control unit 104 may further calculate the pulse rate.

In the present embodiment, although the blood pressure is calculated based on pulse wave information obtained in the pressure reduction process, the blood pressure may also be calculated based on pulse wave information obtained in the pressurization process.

Next, the measurement control unit 104 displays measurement results, i.e., the blood pressure value and pulse rate calculated in step S108 in the display unit 40 (step S110).

Then, the measurement control unit 104 stores measurement results in the measurement result storage area (not shown) in the memory 39 (step S112). In the measurement result storage area of the memory 39, measurement data including the date and time of measurement and measured values (maximal blood pressure, minimal blood pressure, and pulse rate) is stored in a record format for each measurement.

This completes a sequence of measurement processing (power-off).

Also after the measurement processing ends, the battery selected in the power supply selection processing (step S102) is continuously selected.

According to the present embodiment, as described above, it is determined whether the residual quantity of the rechargeable battery 51 is present for at least one-time accomplishment of measurement processing upon startup (when power is turned on), and if such a residual quantity is not present, the dry cell 52 is selected. Therefore, a situation can reliably be avoided in which the capacity of the rechargeable battery 51 runs out during measurement and the measurement is stopped.

The above operation is described by taking the rechargeable battery preference mode as an example, but similar processing can also be performed in a mode to use the dry cell 52 preferentially, that is, a dry cell preference mode.

In the present embodiment, the above-described power supply selection processing is only performed upon startup, but the power supply selection processing may also be performed in other timing in any phase that is not related to measurement control of the blood pressure. For example, the power supply selection processing may be performed when charging of the rechargeable battery 51 is completed, the dry cell 52 is inserted, or an instruction of switching control of the power supply by the user is inputted.

Also, in the present embodiment, a sphygmomanometer including an automatic pressurization unit (for example, the pump 33 and the exhaust valve 34) for automatic pressurization and depressurization is taken as an example, but the sphygmomanometer may also include an automatic pressurization unit (for example, a rubber ball) for manual pressurization and depressurization. If a manual pressurization unit is provided, the pump 33, the exhaust valve 34, the pump drive circuit 36, and the valve drive circuit 37 shown in FIG. 3 are not necessary. Instead, the sphygmomanometer only needs to include a rubber ball (not shown) connected to the air bladder 21 via the tube 24.

<First Modification>

Because the sphygmomanometer 1 according to the present embodiment includes the solar battery 50, if the weather is cloudy or rainy, the rechargeable battery 51 may not be charged even if an attempt is made to charge the rechargeable battery 51. Thus, in addition to the voltage of the battery, switching control of the power supply may further be performed based on a weather forecast result.

Figure 7:
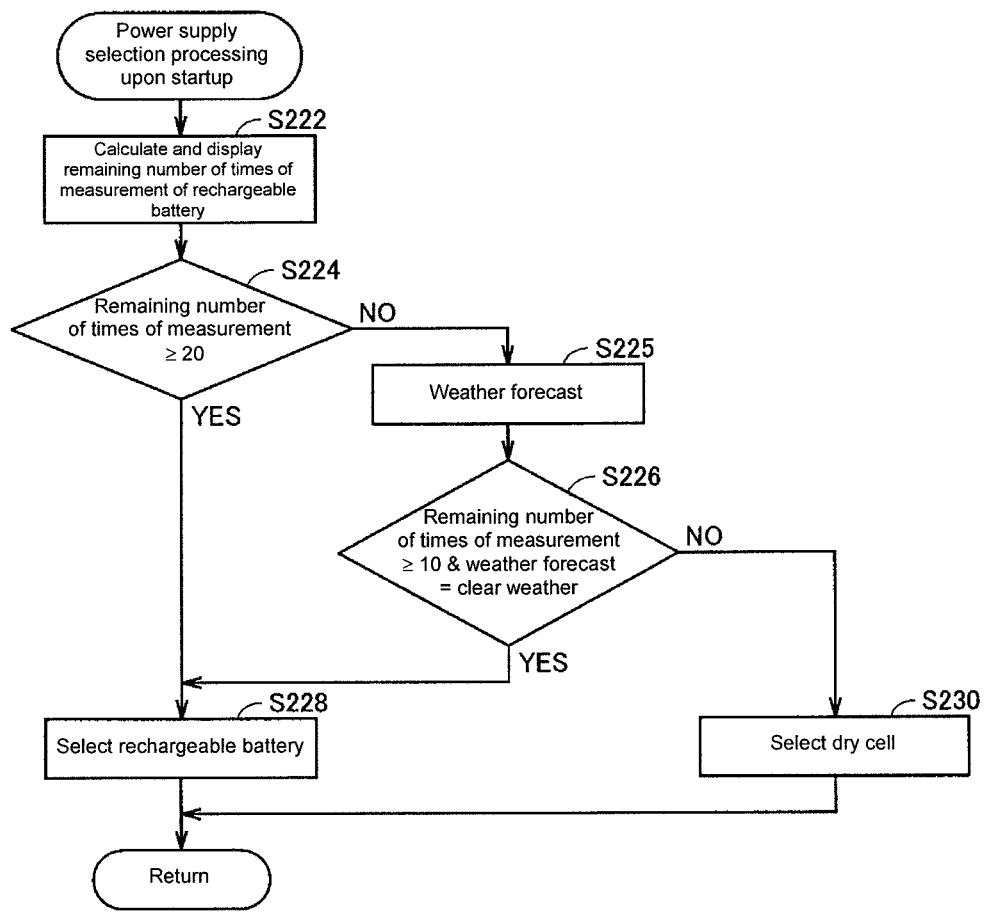
FIG. 7 is a flowchart showing the power supply selection processing according to a first modification of the first embodiment of the present invention.

FIG. 7 is a flowchart showing the power supply selection processing according to the first modification of the first embodiment of the present invention.

In FIG. 7, instead of the voltage, the remaining number of times of measurement that can be made (referred to as the "remaining number of times of measurement") is used as the characteristic value related to the residual quantity of the battery.

In the present example, it is assumed that the number of times of measurement of a person to be measured per day is 10 times.

Referring to FIG. 7, the switching control unit 102 calculates the remaining number of times of measurement of the rechargeable battery 51 and displays in the display unit 40 (step S222). The remaining number of times of measurement is calculated based on, for example, the voltage of the rechargeable battery 51 and a data table (stored in the memory 39) defining the relationship between the voltage and the number of times of measurement in advance. Thus, the characteristic value (remaining number of times of measurement) in the present modification is a value computed by the CPU 100 based on the output from the voltage detectors 56, 57.

Next, the switching control unit 102 determines whether the calculated remaining number of times of measurement is 20 times or more (step S224). If the remaining number of times of measurement is 20 times or more (YES in step S224), the process proceeds to step S228. On the other hand, if the remaining number of times of measurement is less than 20 times (NO in step S224), the process proceeds to step S225.

In step S225, the switching control unit 102 performs forecast processing of the weather. The switching control unit 102 makes a weather forecast by using the pressure sensor 32. The pressure sensor 32 detects an absolute value or relative value of the atmospheric pressure.

It is assumed that the switching control unit 102 periodically receives a signal from the oscillation circuit 35 to record a trend of the absolute value or relative value of the atmospheric pressure on the memory 39. Then, for every predetermined time (for example, six hours), the switching control unit 102 forecasts the weather in the future (for example, the weather three hours later) based on the trend of the absolute value or relative value of the atmospheric pressure. The forecasting method of the weather may adopt a publicly known method.

Next, the switching control unit 102 determines whether the remaining number of times of measurement is 10 times or more and the weather forecast is clear weather (step S226). If the conditions are met (YES in step S226), the process proceeds to step S228. On the other hand, if the conditions are not met (NO in step S226), the processing proceeds to step S230.

In step S228, the switching control unit 102 selects the rechargeable battery 51. The switching control unit 102 sends a switching signal to the switching unit 58 only when the dry cell 52 is selected while power is turned off.

In step S230, the switching control unit 102 selects the dry cell 52. The switching control unit 102 sends a switching signal to the switching unit 58 only when the rechargeable battery 51 is selected while power is turned off.

When the processing in step S228 or step S230 ends, the power supply selection processing is completed.

The thresholds (20 times, 10 times) used to determine the remaining number of times of measurement may be fixed (predetermined value) or may be set based on measurement data recorded in the memory 39. In the latter case, the switching control unit 102 calculates the average number of times of measurement of a person to be measured per day and may set the first threshold (step S224) for two days and the second threshold (step S226) for one day.

Alternatively, the user may be able to directly set or change the two thresholds.

In the present modification, although the remaining number of times of measurement is used as a characteristic value related to the residual quantity of a battery, the voltage of a battery may be used similar to the first embodiment.

<Second Modification>

While the characteristic value related to the residual quantity of a battery corresponds to the voltage in the first embodiment and the remaining number of times of measurement in the first modification of the first embodiment, the voltage level may be represented.

Switching control of the power supply based on the voltage level of the rechargeable battery 51 will be described below. For simplification of the description, the second modification is described by comparing with the first modification.

Figure 8:
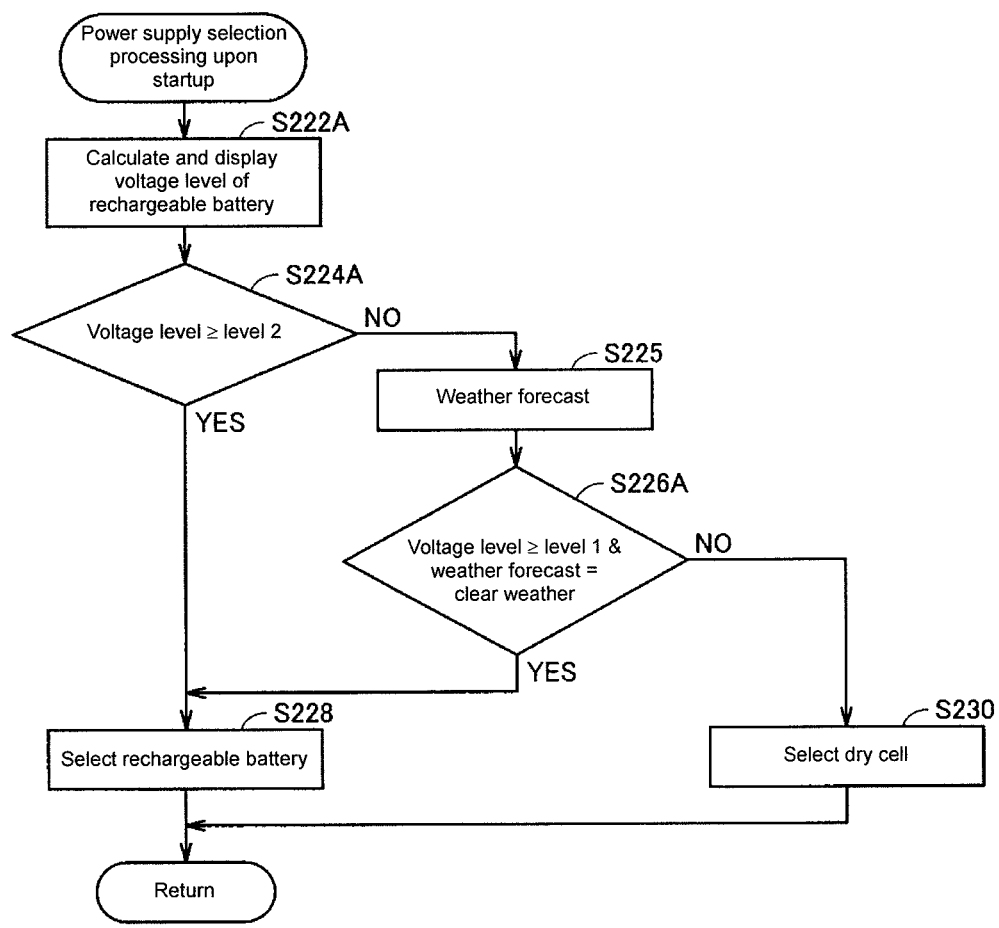
FIG. 8 is a flowchart showing power supply selection processing according to a second modification of the first embodiment of the present invention.

FIG. 8 is a flowchart showing the power supply selection processing according to the second modification of the first embodiment of the present invention. In FIG. 8, the same step number is attached to processing similar to the power supply selection processing shown in FIG. 7. Thus, the descriptions thereof will not be repeated.

In the second modification of the first embodiment, instead of steps S222, S224, and S226 in FIG. 7, steps S222A, S224A, and S226A are performed.

In step S222A, the switching control unit 102 calculates the voltage level of the rechargeable battery 51 and displays in the display unit 40. The voltage level is calculated based on, for example, the voltage of the rechargeable battery 51 and a data table (stored in the memory 39) defining the relationship between the voltage and the voltage level (for example, level 0 to level 3). Thus, the characteristic value (voltage level) in the present embodiment is also a value operated by the CPU 100 based on the output from the voltage detectors 56, 57.

Figure 9:
FIG. 9 is a diagram showing a display example of a voltage level of a rechargeable battery (secondary battery).
Figure 9:
Figure 9:
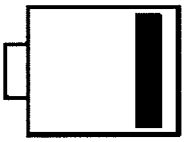
Figure 9:

FIG. 9 is a diagram showing a display example in accordance with the voltage level of the rechargeable battery 51.

In step S224A, the switching control unit 102 determines whether the voltage level of the rechargeable battery 51 is level 2 or higher.

In step S226A, the switching control unit 102 determines whether the voltage level of the rechargeable battery 51 is level 1 or higher and the weather forecast is clear weather.

The first embodiment and the second modification may be combined. That is, the switching control unit 102 may not have to make a weather forecast.

The user may be able to select the characteristic value from the remaining number of times of measurement and the voltage level. Accordingly, the power supply can be switched in desired timing for each user. Moreover, the desired characteristic value is displayed directly or indirectly and thus, user visibility can be improved.

[Second Embodiment]

In the first embodiment and the first and second modifications, switching control of the power supply is performed only once upon startup. In the present embodiment, by contrast, the switching control of the power supply is performed a plurality of number of times in timing related to the measurement processing of the blood pressure.

The configuration in the present embodiment and the basic operation thereof are similar to those in the first embodiment. Therefore, only differences from the first embodiment will be described below by taking the sphygmomanometer 1 shown in FIGS. 1 to 4 as an example. The sphygmomanometer 1 in the present embodiment is assumed to include an automatic pressurization unit.

In the following description, it is assumed that information indicating a dry cell preference mode (mode in which the dry cell 52 is preferentially used if the dry cell 52 is inserted) is stored in the memory 39.

Figure 10:
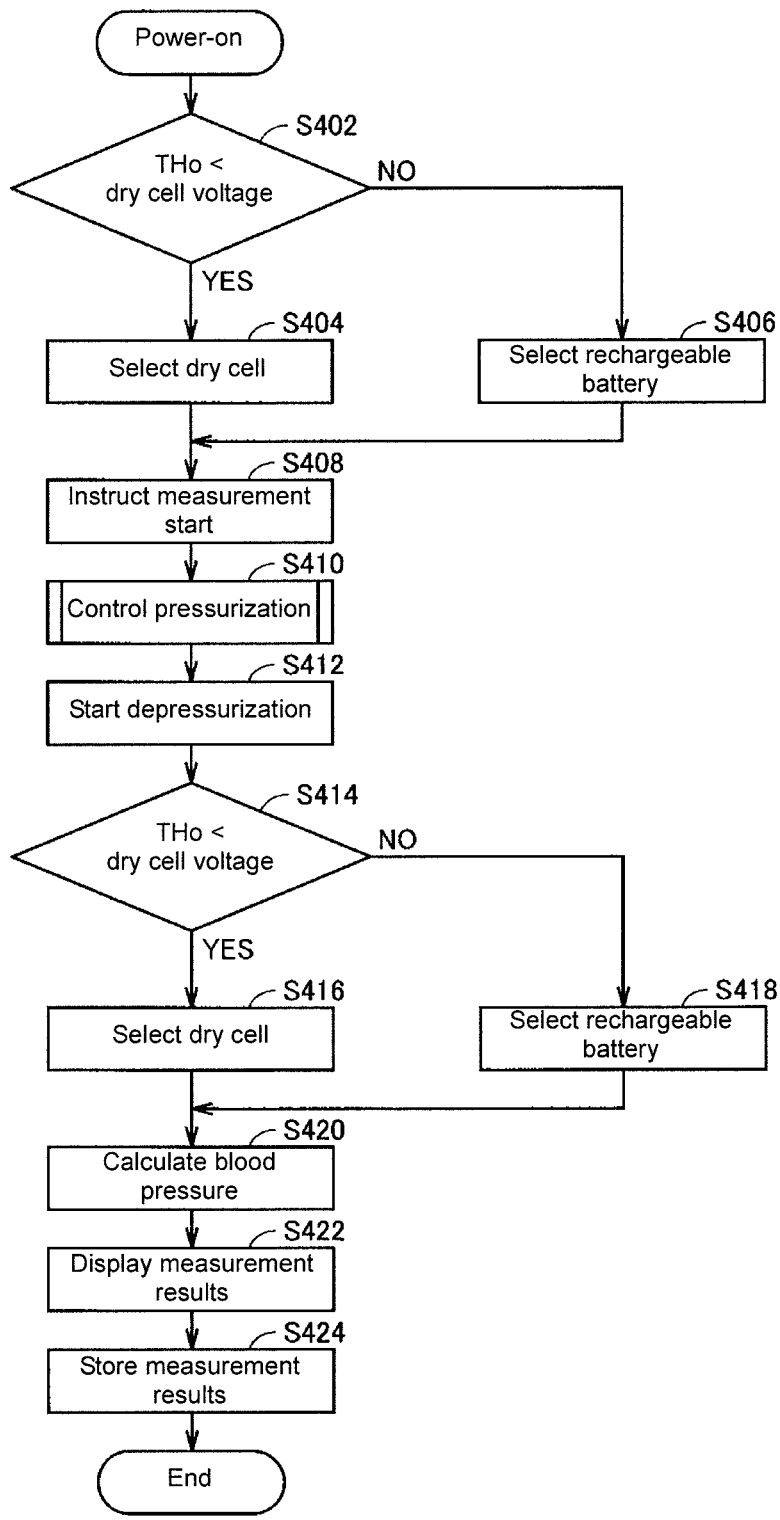
FIG. 10 is a flowchart showing the measurement related processing according to a second embodiment of the present invention.

FIG. 10 is a flowchart showing the measurement related processing according to the second embodiment of the present invention. The processing shown in the flowchart of FIG. 10 is also stored in the memory 39 as a program in advance and the CPU 100 reads and executes the program.

Referring to FIG. 10, if the power switch 41A is pressed, the switching control unit 102 first performs the power supply selection processing (steps S402, S404, S406) upon startup.

It is assumed that the dry cell 52 is selected by the switching unit 58 when the processing started. It is also assumed that the rechargeable battery 51 has a sufficient residual quantity. That is, the voltage of the rechargeable battery 51 obtained from the voltage detector 56 is assumed to be equal to or more than the threshold THm described in the first embodiment.

In step S402, the switching control unit 102 determines whether the voltage of the dry cell 52 is larger than a threshold THo (for example, 4.1 V). The threshold THo represents, for example, a voltage value that can make the sphygmomanometer 1 operable at the very least (for example, the display unit 40 or the operation unit 41 can be enabled). That is, this means that even if the voltage of the dry cell 52 is at about the threshold THo, it is impossible to pressurize up to an appropriate value (for example, 180 mmHg) by the dry cell 52 alone.

If the voltage of the dry cell 52 is larger than the threshold THo (YES in step S402), the switching control unit 102 selects the dry cell 52 (step S404).

On the other hand, if the voltage of the dry cell 52 is equal to or less than the threshold THo (NO in step S402), the switching control unit 102 selects the rechargeable battery 51 (step S406). In this case, the switching control unit 102 performs switching processing of the power supply. That is, the switching control unit 102 sends a control signal to the switching unit 58 to select the rechargeable battery 51.

In the present embodiment as well, the switching control unit 102 displays which of the rechargeable battery 51 and the dry cell 52 is the battery in use in the display unit 40. The same also applies in the following power supply selection processing.

Next, an instruction to start measurement is inputted by the user (step S408).

Thereupon, pressurization control is performed (step S410). The pressurization control will be described as a subroutine in FIG. 11.

Figure 11:
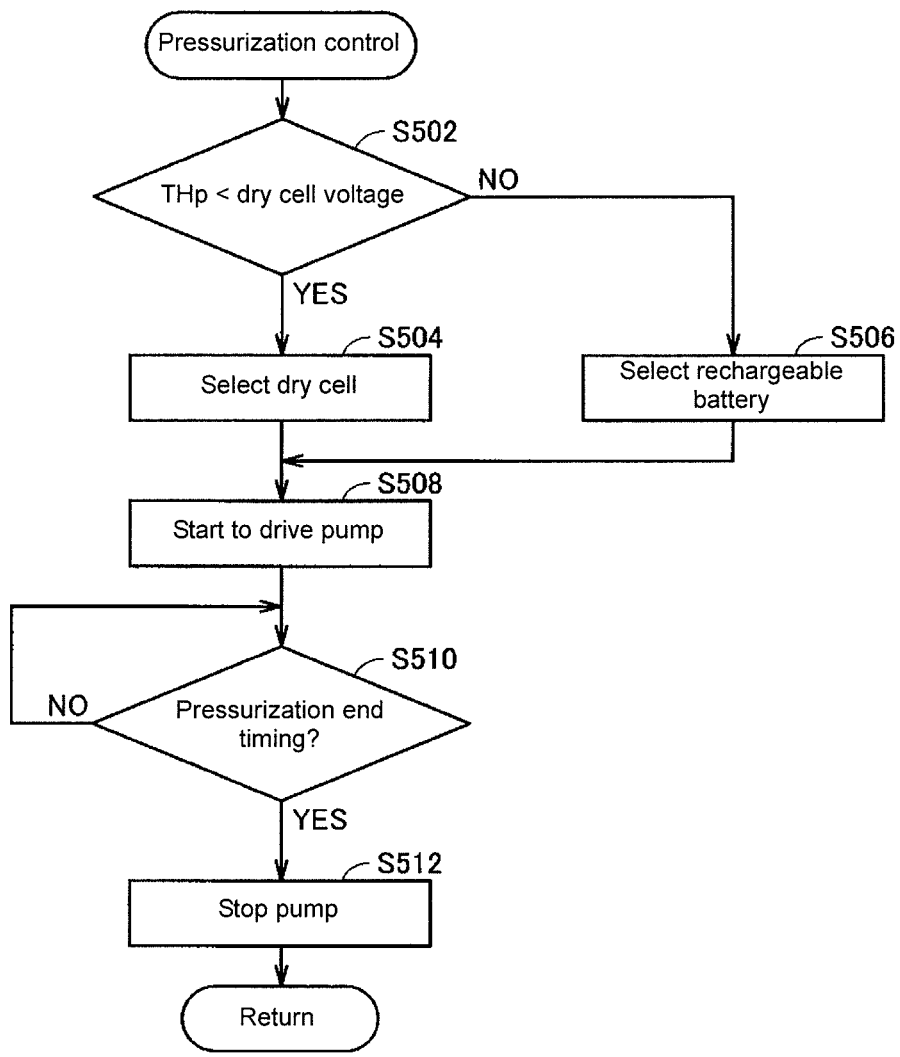
FIG. 11 is a flowchart showing pressurization control according to the second embodiment of the present invention.

FIG. 11 is a flowchart showing the pressurization control according to the second embodiment of the present invention.

Referring to FIG. 11, the switching control unit 102 first performs the power supply selection processing (steps S502, S504, S508) immediately before driving the pump.

In step S502, the switching control unit 102 determines whether the voltage of the dry cell 52 is larger than a preset threshold THp (for example, 4.5 V). The threshold THp is a value sufficiently larger than the threshold THo (operable voltage) upon startup and represents the voltage value (+predetermined value) necessary for driving the pump 33.

If the voltage of the dry cell 52 is larger than the threshold THp (YES in step S502), the switching control unit 102 selects the dry cell 52 (step S504). On the other hand, if the voltage of the dry cell 52 is equal to or less than the threshold THp (NO in step S502), the switching control unit 102 selects the rechargeable battery 51 (step S506).

After one of the batteries is selected as the power supply, the measurement control unit 104 starts to drive the pump 33 to gradually raise the pressure of the air bladder 21 (step S508).

Then, the measurement control unit 104 determines whether pressurization end timing has come (step S510). Here, for example, whether the cuff pressure has reached a predetermined value (for example, 180 mmHg) is determined. The time point when the maximal blood pressure is estimated during pressurization by a publicly known method may be adopted as the pressurization end timing.

Pressurization is continued until the pressurization end timing comes (NO in step S510).

When the pressurization end timing comes (YES in step S510), the measurement control unit 104 stops driving the pump 33 (step S512). When this processing ends, the processing returns to the main routine.

Referring to FIG. 10 again, the measurement control unit 104 starts depressurization (step S412).

At the same time, the switching control unit 102 performs the power supply selection processing (steps S414, S416, S418) at the start of depressurization (immediately after stopping the pump).

Processing in steps S414, S416, S418 may be similar to processing in steps S402, S404, S406 upon startup, respectively. Thus, the descriptions thereof will not be repeated.

When the power supply selection processing at the end of pressurization ends, the measurement control unit 104 calculates blood pressures (maximal blood pressure, minimal blood pressure) and the pulse rate by a publicly known method (step S420).

When the blood pressures are calculated, the measurement control unit 104 displays measurement results in the display unit 40 (step S422). The measurement control unit 104 also stores measurements results in the measurement result storage area (not shown) of the memory 39 (step S424).

Processing in steps S420, S422, S424 may be similar to processing in steps S108, S110, S112 in FIG. 5 according to the first embodiment, respectively.

This completes a sequence of measurement related processing (power-off).

Figure 12:
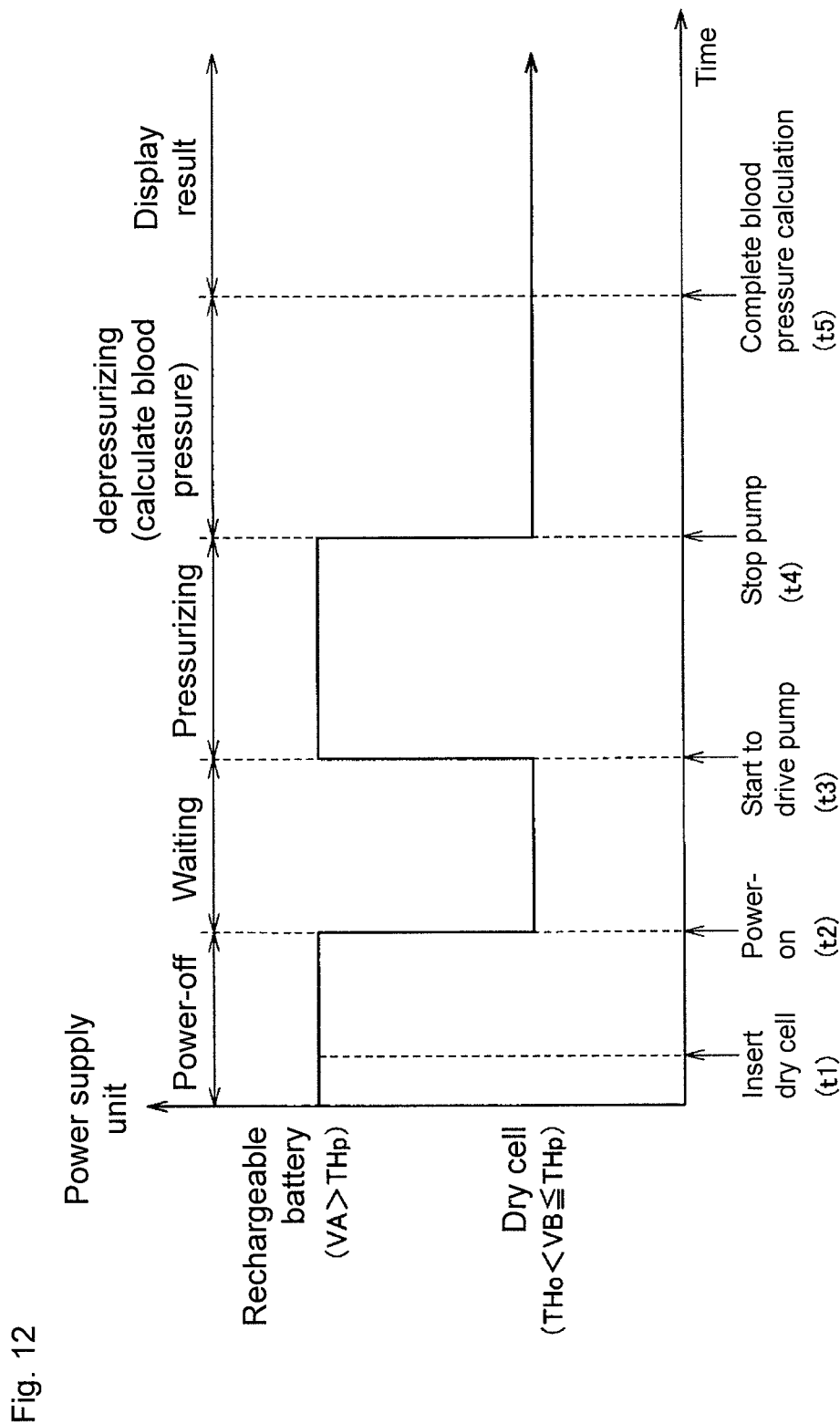
FIG. 12 is a timing chart showing power supply switching timing according to the second embodiment of the present invention.

FIG. 12 is a timing chart showing power supply switching timing according to the second embodiment of the present invention. Also in this timing chart, an example of the dry cell preference mode is shown.

In this timing chart, it is assumed that the voltage VA of the rechargeable battery 51 is larger than the threshold THp and the voltage VB of the dry cell 52 is larger than the threshold THo and equal to or less than the threshold THp.

Referring to FIG. 12, if the dry cell 52 is not inserted into the sphygmomanometer 1, the rechargeable battery 51 is selected as the power supply.

Assume that the dry cell 52 is inserted by the user (time t1) and the power switch 41A is first pressed (time t2). In this case, the voltage VB of the dry cell 52 is larger than the threshold THo, which is the operable voltage (YES in step S402 in FIG. 10), the power supply is switched from the rechargeable battery 51 to the dry cell 52 (step S404 in FIG. 10).

The voltage VB of the dry cell 52 is equal to or less than the threshold THp for pressurization operation (NO in step S502 in FIG. 11) and thus, the power supply is changed from the dry cell 52 to the rechargeable battery 51 when driving of the pump 33 is started (time t3) (step S506 in FIG. 11). Accordingly, the residual quantity of the rechargeable battery 51 is consumed to drive the pump 33.

When driving of the pump 33 is stopped (time t4), the power supply is switched from the rechargeable battery 51 to the dry cell 52 again (YES in step S414 in FIG. 10, S416).

Thus, according to the present embodiment, even if the residual quantity of the dry cell 52 is less than the quantity sufficient for driving the pump 33, the dry cell 52 can be selected as the power supply in any phase other than driving of the pump 33. As a result, the residual quantity of the dry cell 52 can be used efficiently. It is difficult to use up the dry cell 52 in a sphygmomanometer of the automatic pressurization type, but according to the present embodiment, the dry cell 52 can be used up.

In the foregoing, the dry cell preference mode is taken as an example, but in the rechargeable battery preference mode as well, the life of the rechargeable battery 51 can be increased by using up the rechargeable battery 51 to the lower limit.

While the power supply selection processing is not performed when the dry cell 52 is inserted (t1) in the present embodiment, the power supply selection processing may also be performed at t1.

Also, the power supply selection processing may be performed not only when the pump is stopped (t4), but also when the calculation of blood pressure is completed (t5). Time t5 corresponds to the time when depressurization ends.

Alternatively, in the present embodiment, the power supply selection processing is performed only in specific timing, however, the power supply selection processing may be performed periodically while the sphygmomanometer 1 operates by monitoring voltage values of the both batteries 51, 52 periodically. In this manner, the batteries can be used more efficiently.

It should be noted that the second embodiment and the first modification or second modification of the first embodiment may be combined.

<Modification>

In the second embodiment, the power supply is fixed to the battery determined immediately before the pump is driven in a period of pressurization. However, in a period of pressurization, power is consumed most when driving of the pump 33 is started. Thus, to sufficiently use up the preferential battery (the battery to be used preferentially), whether to switch to the preferential battery may be determined when a certain period passes after driving of the pump 33 is started.

In a modification of the second embodiment, the selection processing of the battery is performed also in the period of pressurization.

Figure 13:
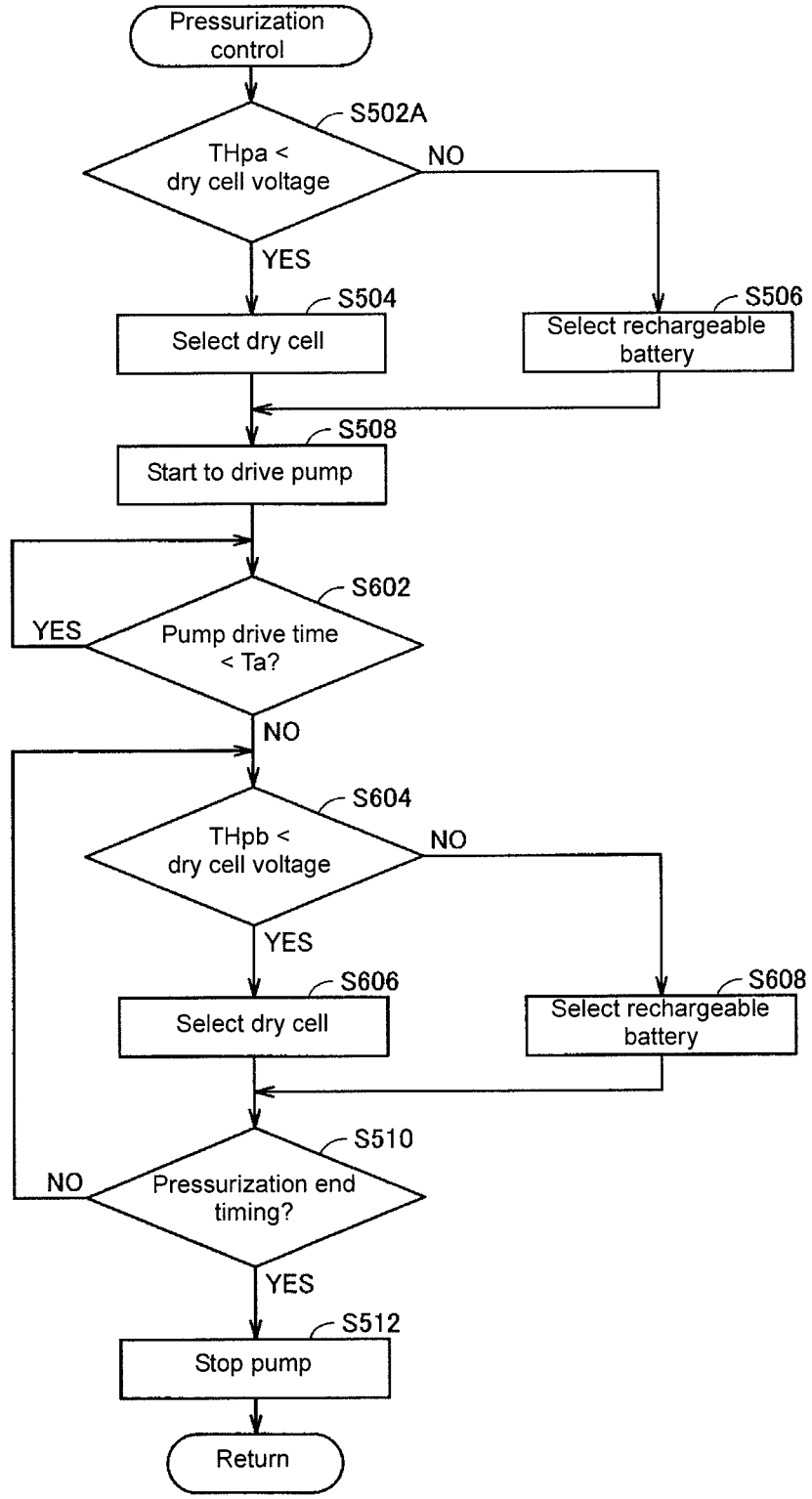
FIG. 13 is a flowchart showing pressurization control according to a modification of the second embodiment of the present invention.

FIG. 13 is a flowchart showing the pressurization control according to the modification of the second embodiment of the present invention. In FIG. 13, the same step number is attached to processing similar to the flowchart shown in FIG. 11 used in the second embodiment. Thus, the descriptions thereof will not be repeated.

Referring to FIG. 13, processing in step S502A is performed, instead of step S502 in FIG. 11. Also, processing of steps S602 to S608 is inserted between step S508 and step S510 in FIG. 11.

In step S502A, the switching control unit 102 determines whether the voltage of the dry cell 52 is larger than a preset threshold THpa (for example, 4.5 V). The threshold THpa represents the voltage value (+predetermined value) necessary for initially driving the pump 33. THpa may be smaller than the threshold THp in the second embodiment, but is sufficiently larger than the threshold THo upon startup.

When driving of the pump 33 is started in step S508, the switching control unit 102 determines whether the elapsed time after starting to drive the pump 33 (that is, the pump drive time) is less than a predetermined time Ta (step S602). The pump drive time may be calculated based on output (the current date, hour, minute, and second) from the timing unit 43. Alternatively, the pump drive time may be counted by a timer (not shown).

The voltage drops considerably when driving of the pump 33 is started (and immediately thereafter). In step S602, whether the voltage of the battery in use has recovered is determined. Instead of the determination of the predetermined time Ta, whether the voltage of the battery in use has returned to the threshold THpa in the initial driving may be determined.

A determination that the pump drive time is equal to or more than the predetermined time Ta is waited for (YES in step S602).

If the pump drive time is determined to be equal to or more than the predetermined time Ta (NO in step S602), the switching control unit 102 determines whether the voltage of the dry cell 52 is larger than a threshold THpb (for example, 4.2 V) (step S604). The threshold THpb represents the voltage value (+predetermined value) necessary to continue driving of the pump 33. The threshold THpb is a smaller value than the threshold THpa in the initial pressurization. The threshold THpb is also a value equal to or larger than the threshold THo upon startup.

If the voltage of the dry cell 52 is determined to be larger than the threshold THpb (YES in step S604), the switching control unit 102 selects the dry cell 52 (step S606). On the other hand, if the voltage of the dry cell 52 is determined to be equal to or smaller than the threshold THpb (NO in step S604), the switching control unit 102 selects the rechargeable battery 51 (step S608).

After one of the batteries is selected, in step S510 described above, whether the pressurization end timing has come is determined. If the pressurization end timing has not come (NO in step S510), the switching control unit 102 returns to step S604. If the pressurization end timing has come (YES in step S510), the switching control unit 102 stops the pump 33 in step S512 described above.

Figure 14:
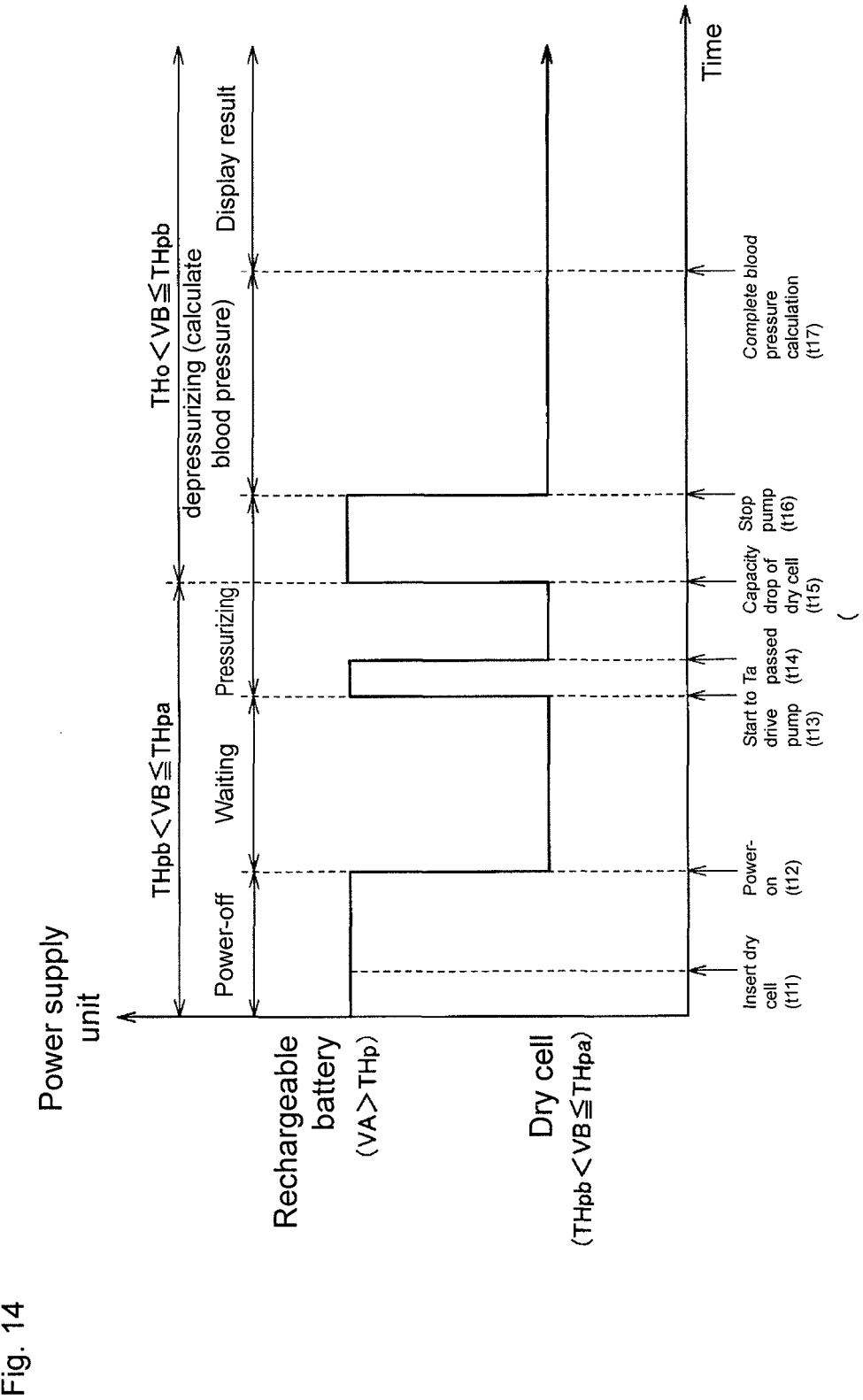
FIG. 14 is a timing chart showing power supply switching timing according to the modification of the second embodiment of the present invention.

FIG. 14 is a timing chart showing the power supply switching timing according to the modification of the second embodiment of the present invention. Also in this chart, an example of the dry cell preference mode is shown.

In this timing chart, it is assumed that the voltage VA of the rechargeable battery 51 is larger than the threshold THp (voltage at which the pump 33 can be driven) used in the second embodiment. It is also assumed that when the timing chart is started, the voltage VB of the dry cell 52 is larger than the threshold THpb (continuation enabling voltage) and equal to or less than the threshold THpa (initial driving voltage).

Referring to FIG. 14, states at times t11 to t13 are similar to those at times t1 to t3 in FIG. 12, respectively. States at times t16, t17 are similar to those at times t4, t5 in FIG. 12, respectively. Thus, detailed descriptions of the states in the above timing will not be repeated.

When driving of the pump 33 is started (t13), the rechargeable battery 51 is selected (step S506 in FIG. 13).

When an initial pressurization time (predetermined time Ta) passes (t14) after driving of the pump 33 is started, the voltage of the dry cell 52 is larger than the threshold THpb (continuation enabling voltage) and thus, the power supply is switched from the rechargeable battery 51 to the dry cell 52 (YES in step S604 in FIG. 13, S606).

Subsequently, it is assumed that the capacity (residual quantity) of the dry cell 52 drops in the process of pressurization (time t15). That is, it is assumed that the voltage value VB of the dry cell 52 becomes equal to or less than the threshold THpb. Then, the power supply is switched from the dry cell 52 to the rechargeable battery 51 again (NO in step S604, S608).

The rechargeable battery 51 remains selected until the pump 33 is stopped.

When driving of the pump 33 is stopped (time t16), the power supply selection processing is performed again. It is assumed that the voltage VB of the dry cell 52 is equal to or less than the threshold THpb, but is larger than the operable voltage THpo. In this case, the power supply is changed again from the rechargeable battery 51 to the dry cell 52, which is the preferential battery (YES in step S414 in FIG. 10, S416).

As described above, according to the modification of the second embodiment, the power supply can be switched also in a period of pressurization.

Therefore, the preferential battery can be used preferentially.

[Third Embodiment]

In each of the above embodiments, the power supply selection processing (switching control) is performed in connection with measurement control of the blood pressure.

In the present embodiment, by contrast, the power supply selection processing is performed in connection with alarm control.

Figure 15:
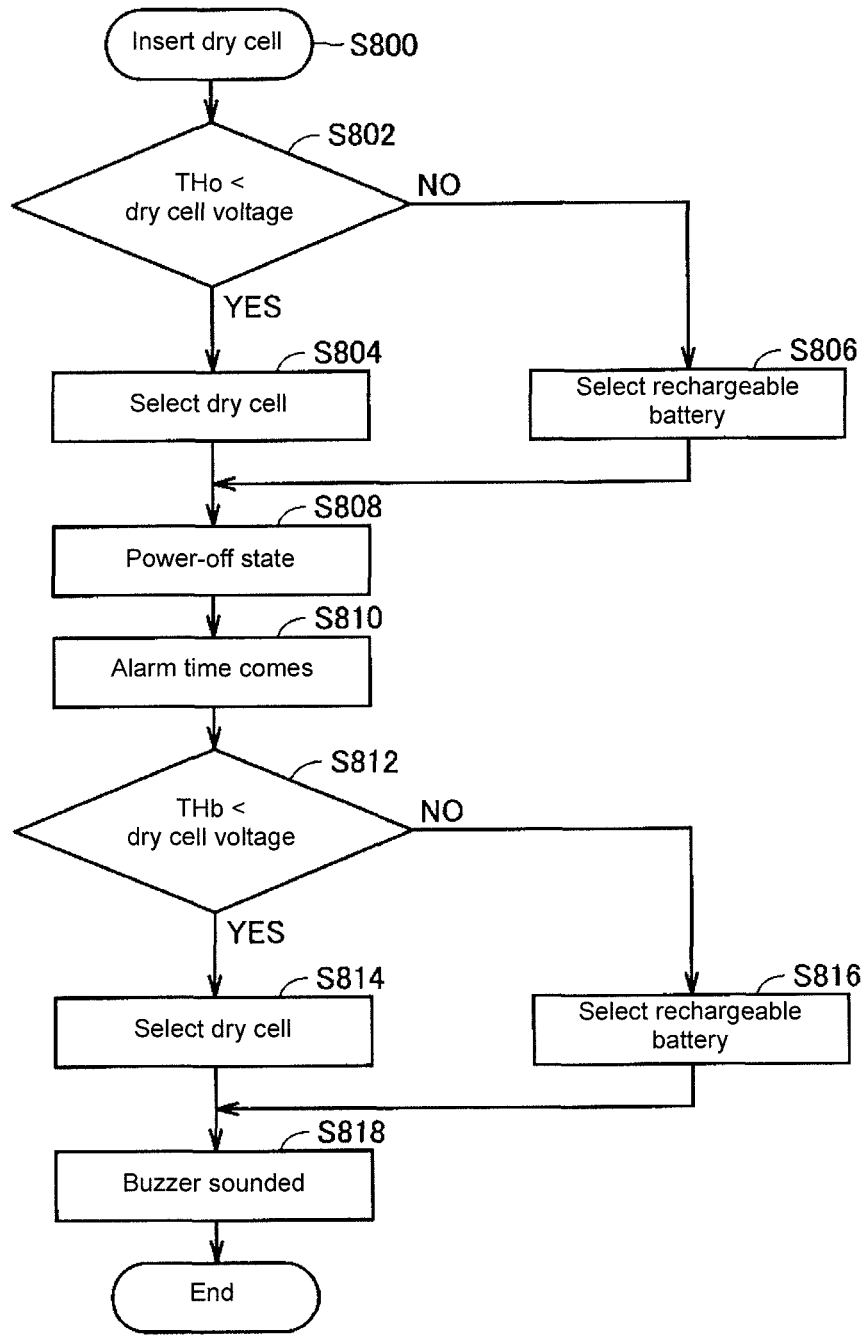
FIG. 15 is a flowchart showing alarm processing according to a third embodiment of the present invention.

FIG. 15 is a flowchart showing alarm processing according to the third embodiment of the present invention. The processing shown in the flowchart of FIG. 15 is also stored in the memory 39 as a program in advance, and the function of the alarm processing is realized by the program being read and executed by the CPU 100.

Also in this example, the dry cell preference mode is assumed to be set.

Referring to FIG. 15, it is assumed that the processing is performed when the dry cell 52 is inserted. Without being restrictive, instead of or in addition to this, the processing may also be performed when charging of the rechargeable battery 51 is completed or an instruction of switching control of the power supply by the user is inputted.

When the dry cell 52 is inserted (step S800), the switching control unit 102 determines whether the voltage of the dry cell 52 is larger than the threshold THo (step S802).

If the voltage of the dry cell 52 is determined to be larger than the threshold THo (YES in step S802), the switching control unit 102 selects the dry cell 52 (step S804). On the other hand, if the voltage of the dry cell 52 is determined to be equal to or smaller than the threshold THo (NO in step S802), the switching control unit 102 selects the rechargeable battery 51 (step S806).

After one of the batteries is selected by the switching control unit 102, the sphygmomanometer 1 is turned off (step S808).

The switching control unit 102 determines whether an alarm time recorded in the memory 39 has come (step S810). In this case, whether the current time obtained from the timing unit 43 is before the alarm time by a predetermined time (for example, 10 seconds) is actually determined.

If the switching control unit 102 determines that the alarm time has come, the switching control unit 102 performs the power supply selection processing.

More specifically, the switching control unit 102 determines whether the voltage of the dry cell 52 is larger than a threshold THb (for example, 4.3 V) (step S812). The threshold THb is a voltage (+predetermined value) necessary to drive the buzzer 44 and is larger than the threshold THo, which is the operable voltage.

If the voltage of the dry cell 52 is determined to be larger than the threshold THb (YES in step S812), the switching control unit 102 selects the dry cell 52 (step S814). On the other hand, if the voltage of the dry cell 52 is determined to be equal to or smaller than the threshold THb (NO in step S812), the switching control unit 102 selects the rechargeable battery 51 (step S816).

When the alarm time recorded in the memory 39 comes, the alarm control unit 106 causes (operates) the buzzer 44 to sound (step S818). As a result, the buzzer 44 generates an alarm sound.

This completes the alarm processing.

Figure 16:
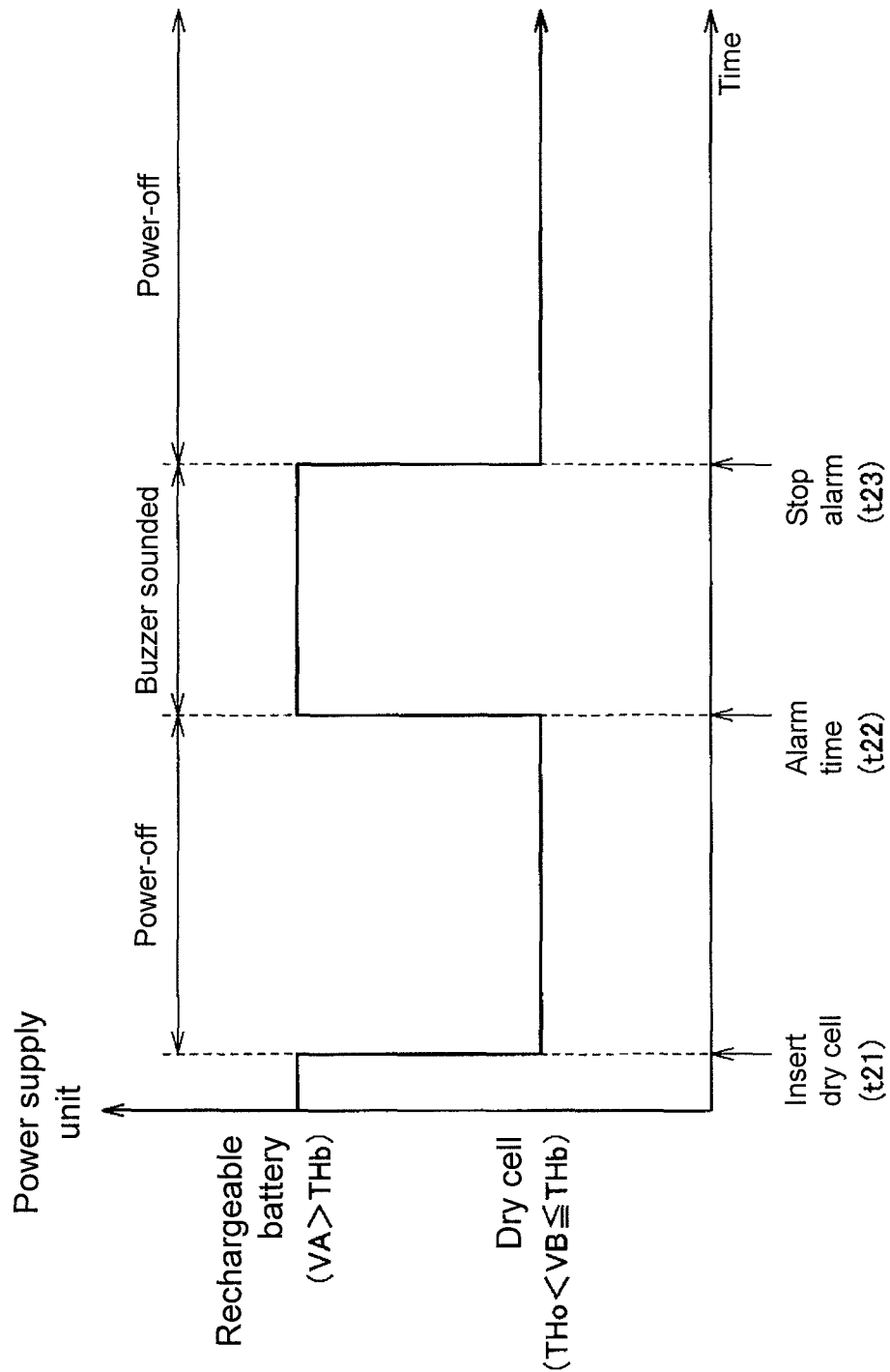
FIG. 16 is a timing chart showing power supply switching timing for the alarm processing according to the third embodiment of the present invention.

FIG. 16 is a timing chart showing the power supply switching timing for the alarm processing according to the third embodiment of the present invention. Also in this timing chart, an example of the dry cell preference mode is shown.

In this timing chart, it is assumed that the voltage VA of the rechargeable battery 51 is larger than the threshold THb and the voltage VB of the dry cell 52 is larger than the threshold THo and equal to or less than the threshold THb.

Referring to FIG. 16, when the dry cell 52 is inserted into the sphygmomanometer 1 (time t21), the voltage of the dry cell 52 is larger than the threshold THo and thus, the power supply is switched from the rechargeable battery 51 to the dry cell 52 (YES in step S802 in FIG. 15, S804).

The sphygmomanometer 1 is turned off after the insertion of the dry cell 52 until the alarm time (time t22) comes.

When the alarm time comes, the voltage of the dry cell 52 is equal to or less than the voltage value THb that enables the buzzer 44 to operate and thus, the rechargeable battery 51 is selected as the power supply again (NO in step S812 of FIG. 15, S816) at this point.

When the alarm is stopped (time t23), the dry cell 52 is selected again.

It should be noted that the third embodiment and the first modification or second modification of the first embodiment may be combined.

In each of the above embodiments, the voltage value of the battery other than the preferential battery (hereinafter, referred to as an "auxiliary battery") is assumed to be sufficiently large, but if the voltage value of the auxiliary battery is equal to or less than various thresholds, the rechargeable battery 51 may be prompted to be quickly charged by an AC adapter.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS

1 Electronic sphygmomanometer
10 Main body portion
20 Cuff
21 Air bladder
24 Air tube
25 Air system
32 Pressure sensor
33 Pump
34 Exhaust valve
35 Oscillation circuit
36 Pump drive circuit
37 Valve drive circuit
39 Memory
40 Display unit
41 Operation unit
41A Power switch
41B Measurement switch
41C Memory switch
43 Timing unit
44 Buzzer
50 Solar battery
51 Rechargeable battery
52 Dry cell
53 Power supply control circuit
56, 57 Voltage detector
58 Switching unit
60 Power supply unit
100 CPU
102 Switching control unit
104 Measurement control unit
106 Alarm control unit

The invention claimed is:

1. An electronic sphygmomanometer adapted to measure a blood pressure of a person to be measured, comprising:
a cuff to be wrapped around a predetermined body site of the person to be measured;
a pressure sensor that detects a pressure inside the cuff;
a measurement controller that controls a blood pressure measurement of the person to be measured based on a signal from the pressure sensor;
a power supplier comprising a primary battery and a secondary battery;
a voltage detector that detects a voltage of the primary battery;
a pressurizer that pressurizes the cuff using power supplied from the power supplier;
a switching controller that selects a supply source of the power to operate the electronic sphygmomanometer by switching the primary battery and the secondary battery, wherein the switching controller firstly compares the voltage of the primary battery detected by the voltage detector with a first threshold upon startup of the electronic sphygmomanometer, selects the primary battery when the voltage of the primary battery is greater than the first threshold, after the startup and before pressurization by the pressurizer, the switching controller secondly compares the voltage of the primary battery detected by the voltage detector with a second threshold, which is larger than the first threshold and higher than a required voltage necessary to drive the pressurizer, and selects the secondary battery when the voltage of the primary battery is less than the second threshold.

2. The electronic sphygmomanometer according to claim 1, wherein the switching controller makes a weather forecast based on the signal from the pressure sensor and selects the primary battery or the secondary battery based on a weather forecast result.

3. The electronic sphygmomanometer according to claim 2, wherein when the voltage of the secondary battery is larger than a first threshold upon startup of the electronic sphygmomanometer, the switching controller selects the secondary battery, and when the voltage of the secondary battery is equal to or smaller than the first threshold, the switching controller selects the primary battery or the secondary battery in accordance with the weather forecast result.

4. The electronic sphygmomanometer according to claim 1,
wherein when the voltage of the primary battery is larger than the first threshold upon startup of the electronic sphygmomanometer, the switching controller selects the primary battery, and when the voltage of the primary battery is equal to or smaller than the first threshold, the switching controller selects the secondary battery.

5. The electronic sphygmomanometer according to claim 4,
wherein when the primary battery is selected upon startup of the electronic sphygmomanometer, the switching controller further switches from the primary battery to the secondary battery when the switching controller determines that the voltage of the primary battery detected by the voltage detector before pressurization by the pressurizer is equal to or smaller than the second threshold.

6. The electronic sphygmomanometer according to claim 5, wherein when the secondary battery is selected before pressurization, the switching controller further switches from the secondary battery to the primary battery again when the switching controller determines that the voltage of the primary battery during the pressurization by the pressurizer is larger than a third threshold that is smaller than the second threshold.

7. The electronic sphygmomanometer according to claim 1, wherein the switching controller preferentially selects the battery specified by a user in advance of the primary battery and the secondary battery.

8. The electronic sphygmomanometer according to claim 1, further comprising a generator that generates an alarm sound in a specific timing specified by a user,
wherein when the specific timing comes, the switching controller further switches the primary battery and the secondary battery based on the detection result by the voltage detector.

* * * * *